United States Patent [19]
Rafter et al.

[11] Patent Number: 6,121,242
[45] Date of Patent: *Sep. 19, 2000

[54] TREATMENT OF BACTERIAL DYSENTERY

[75] Inventors: David J. Rafter; Bradley G. Thompson, both of Calgary; Peter N. McLaine, Ottawa, all of Canada; Peter C. Rowe, Towson, Md.; Elaine Orrbine, Ottawa, Canada; Terrance P. Klassen, Gloucester, Canada; Glen D. Armstrong, Edmonton, Canada; Paul R. Goodyer, Montreal West, Canada; Andrew M. MacKenzie, Gloucester, Canada; George A. Wells, Ottawa, Canada; Hermy Lior, Nepean, Canada; Francois Auclair, Cumberland, Canada

[73] Assignee: Synsorb Biotech, Inc., Calgary, Canada

[*] Notice: This patent is subject to a terminal disclaimer.

[21] Appl. No.: 09/296,584

[22] Filed: Apr. 23, 1999

Related U.S. Application Data

[63] Continuation of application No. 09/115,637, Jul. 15, 1998, abandoned, which is a continuation of application No. 08/786,930, Jan. 23, 1997, Pat. No. 5,849,714, which is a continuation of application No. 08/669,004, Jun. 21, 1996, abandoned.

[51] Int. Cl.$^7$ .................. A61K 31/70; A61K 31/695

[52] U.S. Cl. .................. 514/25; 514/53; 514/61; 514/63

[58] Field of Search .................. 514/23, 25, 53, 514/61, 63

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 424/11 |
| 4,362,720 | 12/1982 | Lemieux et al. | 424/180 |
| 5,079,353 | 1/1992 | Ratcliffe et al. | 536/53 |
| 5,484,773 | 1/1996 | Heerze et al. | 514/23 |
| 5,620,858 | 4/1997 | Armstrong et al. | 435/7.8 |
| 5,679,653 | 10/1997 | Armstrong et al. | 514/53 |
| 5,849,714 | 12/1998 | Rafter et al. | 514/23 |

FOREIGN PATENT DOCUMENTS

| | | |
|---|---|---|
| 0101027 | 2/1984 | European Pat. Off. . |
| 0305968 | 3/1989 | European Pat. Off. . |
| WO86/04064 | 7/1986 | WIPO . |
| WO91/16072 | 10/1991 | WIPO . |
| WO93/08209 | 4/1993 | WIPO . |
| WO95/29701 | 11/1995 | WIPO . |

OTHER PUBLICATIONS

Armstrong et al., "Use of Carboyhdrate Sequences in Treating Enteric Infections", Abstract Book, XIXth International Carbohydrate Symposium, UCSD (San Diego, CA), abstact CO 004, Aug. 1998.
Abbas, S.Z., et al., "Tumor–Associated Oligosaccharides I: Synthesis of Sialyl–Lewis$^a$ Antigenic Determinant", Sialic Acids, Proc. Japan–German Symp., Berlin:22–23 (1988).
Altman, D.G., et al., *Practical Statistics for Med. Res.*, 1st Ed., New York, Chapman and Hall:179–228 (1991).
Amvam–Zollo, P.H., et al., "Streptococcus pneumoniae Type XIV Polysaccharide: Synthesis of a Repeating Branched Tetrasaccharide with Dioxa–Type Spacer–Arms", *Carbohy. Res.*, 150:199–212 (1986).
Armstrong, G.D., et al., "Maintenance of Biological Activity of Pertussis Toxin Radioiodinated While Bound to Fetuin–Agarose", *Infect. Immun.*, 55(5):1294–1299 (1987).
Armstrong, Glen D., et al., "Investigation of Shiga–Like Toxin Binding to Chemically Synthesized Oligosaccharide Sequences", *J. Infect. Dis.*, 164(6):1160–1167 (1991).
Armstrong, Glen D., et al, "A Phase I Study of Chemically Synthesized Verotoxin (Shiga–Like Toxin) Pk–Trisaccharide Receptors Attached to Chromosorb for Preventing Hemolytic–Uremic Syndrome", *J. Infect. Dis.*, 171(4):1042–1045 (1995).
Boyd, B., et al., "Verotoxin Receptor Glycolipid in Human Renal Tissue", *Nephron*, 51:207–210 (1989).
Calderwood, S.B., et al., "Nucleotide Sequence of the Shiga–Like Toxin Genes of Escherichia coli", *Proc. Natl. Acad. Sci.* (USA), 84:4364–4368 (1987).
Chernyak, A.Y., et al., "A New Type of Carbohydrate–Containing Synthetic Antigen: Synthesis of Carbohydrate–Containing Polyacrylamide Copolymers Having the Specificity of O:3 and O:4 Factors of Salmonella", *Carbohy. Res.*, 128:269–282 (1984).
Cimolai, N., et al., *J. Pediatr.*, 117:676 (1990).
Cohen, A., et al., "Roles of Globotriosyl– and Galabiosylceramide in Verotoxin Binding and High Affinity Interferon Receptor", *J. Biol. Chem.*, 262(35):17088–17091 (1987).
Cox, D.D., et al., "A New Synthesis of 4–O–α–D–Galactopyranosyl–D–Galactopyranose", *Carbohy. Res.*, 62:245–252 (1978).
Dahmen, J., et al., "2–Bromoethyl Glycosides: Applications in the Synthesis of Spacer–Arm Glycosides", *Carbohy. Res.*, 118:292–301 (1983).
Dahmen, J., et al., "Synthesis of Spacer–Arm, Lipid, and Ethyl Glycosides of the Trisaccharide Portion [α–D–Gal–(1→4)–β–D–Gal–(1→4)–β–D–Glc] of the Blood–Group P$^k$ Antigen: Preparation of Neoglycoproteins", *Carbohy. Res.*, 127:15–25 (1984).
DeGrandis, S., et al., "Globotetraosylceramide is Recognized by the Pig Edema Disease Toxin", *J. Biol. Chem.*, 264(21):12520–12525 (1989).
Ekborg, G., et al., "Synthesis of Three Disaccharides for the Preparation of Immunogens Bearing Immunodeterminants Known to Occur on Glycoproteins", *Carbohy. Res.*, 110:55–67 (1982).

(List continued on next page.)

Primary Examiner—Howard C. Lee
Attorney, Agent, or Firm—Burns, Doane, Swecker & Mathis, L.L.P.

[57] ABSTRACT

Disclosed are methods for the neutralization of shiga-like toxins (SLT) associated with enteric *E. coli* infection which methods inhibit progression of this infection into hemolytic uremic syndrome (HUS).

13 Claims, 5 Drawing Sheets

OTHER PUBLICATIONS

Fernandez–Santana, V., et al., "Glycosides of Monoallyl Diethylene Glycol. A New Type of Spacer Group for Synthetic Oligosaccharides", *J. Carbohy. 1Chem.*, 8(3):531–537 (1989).

Fügedi, P., et al., "Thioglycosides as Glycosylating Agents in Oligosaccharide Synthesis", *Glycoconjugate J.*, 4:97–108 (1987).

Gannon, et al., "Molecular Cloning and Nucleotide Sequence of Another Variant of the *Escherichia coli* Shiga–Like Toxin II Family", *J. Genl. Microbiol.*, 136:1125–1135 (1990).

Garegg, P.J., et al., "A Synthesis of 8–Methoxycarbonyloct–1–YL O–α–D–Galactopyranosyl–(1→3)–O–β–D–Galactopyranosyl–(1→4)–2–Acetamido–2–Deoxy–β–D–Glucopyranoside", *Carbohy. Res.*, 136:207–213 (1985).

Garegg, P.J., et al., "Synthesis of 6– and 6'–Deoxy Derivatives of Methyl 4–O–α–D–Galactopyranosyl–β–D–Galactopyranoside for Studies of Inhibition of Pyelonephritogenic Fimbriated *E. coli* Adhesion to Urinary Epithelium–Cell Surfaces", *Carbohy. Res.*, 137:270–275 (1985).

Head. S.C., et al., "Purification and Characterization of Verocytotoxin 2", *FEMS Microbiol. Lett.*, 51:211–216 (1988).

Head, S., et al., "Modification of the Glycolipid–Binding Specificity of Vero Cytotoxin by Polymyxin B and Other Cyclic Amphipathic Peptides", *Infect. Immun.*, 58(6):1532–1537 (1990).

Ito, et al., "Cloning and Nucleotide Sequencing of Vero Toxin 2 Variant Genes from *Escherichia coli* 091:H21 Isolated from a Patient with the Hemolytic Uremic Syndrome", *Microbial Pathog.*, 8:47–60 (1990).

Jacewicz, M., et al., "Pathogenesis of Shigella Diarrhea XI. Isolation of a Shigella Toxin–Biding Glycolipid from Rabbit Jejunum and HeLa Cells and its Identification as Globotriaosylceramide", *J. Exp. Med.*, 163:1391–1404 (1986).

Jackson, M.P., et al., "Nucleotide Sequence Analysis of the Structural Genes for Shiga–Like Toxin I Encoded by Bacteriophage 993J from *Escherichia coli*", *Microbial Pathog.*, 2:147–153 (1987).

Jacquinet, J.C., et al., "Synthesis of Blood–Group Substances. Part 11. Synthesis of the Trisaccharide O–α–D–Galactopyranosyl–(1→3)–O–β–D–Galactopyranosyl–(1→4)–2–Acetamido–2–Deoxy–D–glucopyranose", *J.C.S. Perkin*, I:326–330 (1981).

Kameyama, A., et al., "Total Synthesis of Sialyl Lewis X", *Carbohy. Res.*, 209:c1–c4 (1991).

Karmali, M.A., et al., "Sensitive Method for Detecting Low Numbers of Verotoxin–Producing *Escherichia coli* in Mixed Cultures by Use of Colony Sweeps and Polymyxin Extraction of Verotoxin", *J. Clin. Microbiol.*, 22(4):614–619 (1985).

Koike, K., et al., "Total Synthesis of Globotriaosyl–E and Z–Ceramides and Isoglobotriaosyl–E–Ceramide", *Carbohy. Res.*, 163:189–208 (1987).

Lee, R.T., et al., "Synthesis of 3–(2–Aminoethylthio)Propyl Glycosides", *Carbohy. Res.*, 37:193–201 (1974).

Lemieux, R.U., et al., "The Properties of a 'Synthetic' Antigen Related to the Human Blood–Group Lewis$^a$", *J. Amn. Chem. Soc.*, 97(14):4076–4083 (1975).

Lingwood, C.A., et al., "Glycolipid Binding of Purified and Recombinant *Escherichia coli* Produced Verotoxin in Vitro", *J. Biolog. Chem.*, 262(18):8834–8839 (1987).

Lindberg, A.A., et al., "Identification of the Carbohydrate Receptor for Shiga Toxin Produced by *Shigella dysenteriae* Type 1", *J. Biolog. Chem.*, 262(4):1779–1785 (1987).

Okamoto, K., et al., "Glycosidation of Sialic Acid", *Tetrahedron*, 47:5835–5857 (1990).

Oku, et al., *Microbial Pathog.*, 6:113–122 (1989).

Paulsen, H., "Advances in Selective Chemical Syntheses of Complex Oligosaccharides", *Angew. Chem. Int. Ed. Eng.*, 21(3):155–173 (1982).

Paulsen, H., et al., "Synthese Von Oligosaccharid–Determinanten Mit Amid–Spacer Vom Typ Des T–Antigens", *Carbohy. Res.*, 104:195–219 (1982).

Rana, S.S., et al., "Synthesis of Phenyl 2–Acetamido–2–Deoxy–3–O–α–L–Fucopyranosyl–β–D–Glucopyranoside and Related Compounds", *Carbohy. Res.*, 91:149–157 (1981).

Robson, W.L.M., et al., "Influence of Antidiarrheal and Antimicrobial Medications on the Hemorrhagic Colitis Associated with Hemolytic–Uremic Syndrome", *J. Pediatr.*, 117:675–676 (1990).

Samuel, J.E., et al., "Comparison of the Glycolipid Receptor Specificities of Shiga–Like Toxin Type II and Shiga–Like Toxin Type II Variants", *Infect. Immun.*, 58(3):611–618 (1990).

Schaubach, R., et al., "Tumor–Associated Antigen Synthesis: Synthesis of the Gal–α–(1→3)–Gal–β–(1→4)–GlcNAc Epitope. A Specific Determinant for Metastatic Progression?", *Liebigs Ann. Chem.*, 607–614 (1991).

Schmidt, R.R., "New Methods for the Synthesis fo Glycosides and Oligosaccharides—Are There Alternatives to the Koenigs–Knorr Method?", *Angew. Chem. Int. Ed. Eng.*, 25:212–235 (1986).

Schmitt, C.K., et al., "Two Copies of Shiga–Like Toxin II–Related Genes Common in Enterohemorrhagic *Escherichia coli* Strains Are Responsible for the Antigenic Heterogeneity of the O157:H Strain E32511", *Infect. Immun.*, 59(3):1065–1073 (1991).

Scotland, S.M., et al., "Two Distinct Toxins Active on Vero Cells from Escherichia coli 0157", *Lancet*, ii:885–886 (1991).

Strockbine, N.A., et al., "Cloning and Sequencing of the Genes for Shiga Toxin from *Shigella dysenteriae* Type 1", *J. Bacteriol.*, 170(3):1116–1122 (1988).

Waddell, T., et al., "Globotriosyl Ceramide is Specifically Recognized by the Escherichia coli Verocytotoxin 2", *Biochem. Biophys. Res. Comm.*, 152(2):674–679 (1988).

Waddell, T., et al., "Induction of Verotoxin Sensitivity in Receptor–Deficient Cell Lines Using the Receptor Glycolipid Globotriosylceramide", *Proc. Natl. Acad. Sci. (USA)*, 7898–7901 (1990).

Weinstein, D.L., et al., "Cloning and Sequencing of a Shiga–Like Toxin Type II Variant from an *Escherichia coli* Strain Responsible for Edema Disease of Swine", *J. Bacteriol.*, 170(9):4223–4230 (1988).

TREATMENT OF BACTERIAL DYSENTERY

This application is a continuation of application Ser. No. 09/115,637, filed Jul. 15, 1998 now abandoned, which was a continuation application of application Ser. No. 08/786,930, filed Jan. 23, 1997 now U.S. Pat. No. 5,849,714, which was a continuation application of application Ser. No. 08/669,004, filed Jun. 21, 1996 now abandoned.

BACKGROUND OF THE INVENTION

1. Field of the Invention

This invention relates to the treatment of diarrhea caused by pathogenic *E. coli* infection. More specifically, this invention relates to methods for the neutralization of shiga-like toxins (SLT) associated with enteric *E. coli* infection which methods inhibit progression of this infection into hemolytic uremic syndrome (HUS).

2. References

The following references are cited in the application as numbers in brackets ([]) at the relevant portion of the application.

1. Karmali, M. A. et al., *J. Clin. Microbiol.* 22:614–619 (1985).
2. Head, S., et al., *Infect Immunol.* 58:1532–1537 (1990).
3. Samuel et al., *Infect Immunol.* 58:611–618 (1990).
4. Altman, D. G. *Practical Statistics for Medical Research* 1st ed. New York, Chapman and Hall: 179–228 (1991).
5. Calderwood, et al., *Proc. Natl. Acad. Sci.* (*USA*), 84:4364–4368 (1987)
6. Jackson, et al., *Microb. Pathog.*, 2:147–153 (1987)
7. Strockbine, et al., *J. Bacteriol.*, 170:1116–1122 (1988)
8. Robson, et al., *J. Pediatr.*, 117:675–676 (1990)
9. Cimolai, et al., *J. Pediatr.*, 117:676 (1990)
10. Armstrong, et al., International Patent Application Publication No. WO 93/08209, for "*DIAGNOSIS AND TREATMENT OF BACTERIAL DYSENTERY*, published Apr. 29, 1993.
11. Lemieux, R. U., et al., "The properties of a 'synthetic' antigen related to the blood-group Lewis A", *J. Am. Chem. Soc.*, 97:4076–83 (1975).
12. Lemieux, R. U., et al., "Glycoside-Ether-Ester Compounds", U.S. Pat. No. 4,137,401, issued Jan. 30, 1979.
13. Lemieux, R. U. et al., "Artificial Oligosaccharide Antigenic Determinants", U.S. Pat. No. 4,238,473, issued Dec. 9, 1980.
14. Lemieux, R. U., et al., "Synthesis of 2-Amino-2-Deoxyglycoses and 2-Amino-2-Deoxyglycosides from glycals", U.S. Pat. No. 4,362,720, issued Dec. 7, 1982.
15. Cox, D., et al. "A New Synthesis of 4-O-α-D-Galactopyranosyl-D-Galacto-Pyranose", *Carbohy. Res.*, 62: 245–252 (1978).
16. Dahmén, J., et al., "Synthesis of space arm, lipid, and ethyl glycosides of the trisaccharide portion [α-D-Gal-(1–4-)-β-D-Gal(1–4)-β-D-Glc] of the blood group p$^k$ antigen: preparation of neoglycoproteins", *Carbohydrate Research*, 127: 15–25 (1984).
17. Garegg, P. J., et al., "A Synthesis of 8-Methoxycarbonyloct-1-yl O-α-D-Galactopyranosyl-(1–3)-0-β-D-Galactopyranosyl-(1–4)-2-Acetamide-2-Deoxy-β-D-Glucopyranoside", *Carbohy. Res.*, 136: 207–213 (1985).
18. Garegg. P. J., et al., "Synthesis of 6- and 6'-deoxy derivatives of methyl 4-0-α-D-galactopyranosyl-β-D-galactopyranoside for studies of inhibition of pyelonephritogenic fimbriated *E. coli* adhesion to urinary epithelium-cell surfaces", *Carbohy. Res.*, 137: 270–275 (1985).
19. Jacquinet, J. C., et al., "Synthesis of Blood-group Substances, Part 11. Synthesis of the Trisaccharide O-α-D-Galactopyranosyl-(1–3)-0-β-D-galactopyranosyl-(1–4)-2-acetamide-2-deoxy-D-glucopyranose", *J. C. S. Perkin*, I: 326–330 (1981).
20. Koike, K., et al., "Total Synthesis of Globotriaosyl-E and Z-Ceramides and Isoglobotriaosyl-E-Ceramide," *Carbohydr. Res.*, 163: 189–208 (1987).
21. Schaubach, R., et al., "Tumor-Associated Antigen Synthesis: Synthesis of the Gal-α-(1–3)-Gal-β-(1–4)-GlcNAc Epitope. A specific Determinant for Metastatic Progression?", *Liebigs Ann. Chem.*, 607–614 (1991).
22. Ratcliffe, R. M., et al., "Sialic Acid Glycosides, Antigens, Immunoadsorbents, and Methods for Their Preparation", U.S. Pat. No. 5,079,353, issued Jan. 7, 1992.
23. Okamoto, K., et al., "Glycosidation of Sialic Acid," *Tetrahedron*, 47: 5835–5857 (1990).
24. Abbas, S. A., et al., "Tumor-Associated Oligosaccharides I: Synthesis of Sialyl-Lewis$^a$ Antigenic Determinant", *Sialic Acids, Proc. Japan-German Symp.* Berlin 22–23 (1988).
25. Paulsen, "Advances in Selective Chemical Syntheses of Complex Oligosaccharides", *Angew. Chem. Int. Ed. Eng.*, 21:155–173 (1982).
26. Schmidt, "New Methods for the Synthesis of Glycosides and Oligosaccharides—Are There Alternatives to the Koenigs-Knorr Method?", *Angew. Chem. Int. Ed. Eng.*, 25:212–235 (1986).
27. Fügedi, P., et al., "Thioglycosides as Glycosylating Agents in Oligosaccharide Synthesis", *Glycoconjugate J.*, 4:97–108 (1987).
28. Kameyama, A., et al., "Total synthesis of stialyl Lewis X", *Carbohydrate Res.*, 209: c1–c4 (1991).
29. Ekborg, G., et al., "Synthesis of Three Disaccharides for the Preparation of Immunogens bearing Immunodeterminants Known to Occur on Glycoproteins", *Carbohydrate Research*, 110: 55–67 (1982).
30. Dahmén, J., et al., "2-Bromoethyl glycosides: applications in the synthesis of spacer-arm glycosides", *Carbohydrate Research*, 118: 292–301 (1983).
31. Rana, S. S., et al., "Synthesis of Phenyl 2-Acetamide-2-Deoxy-3-O-α-L-Fucopyranosyl-β-D-Glucopyranoside and Related Compounds", *Carbohydrate Research*, 91:149–157 (1981).
32. Amvam-Zollo, P., et al., "*Streptococcus pneumoniae* Type XIV Polysaccharide: Synthesis of a Repeating Branched Tetrasaccharide with Dioxa-Type Spacer-Arms", *Carbohydrate Research*, 150:199–212 (1986).
33. Paulsen, H., "Synthese von oligosaccharid-determinanten mit amid-spacer vom typ des T-antigens", *Carbohydr. Res.* 104:195–219 (1982).
34. Chernyak, A. Y., et al., "A New Type of Carbohydrate-Containing Synthetic Antigen: Synthesis of Carbohydrate-Containing Polyacrylamide Copolymers having the Specificity of 0:3 and 0:4 Factors of Salmonella", *Carbohydrate Research*, 128:269–282 (1984).
35. Fernandez-Santana, V., et al., "Glycosides of Monoallyl Diethylene Glycol. A New type of Spacer group for Synthetic Oligosaccharides", *J. Carbohydrate Chemistry*, 8(3):531–537 (1989).
36. Lee, R. T., et al., "Synthesis of 3-(2-Aminoethylthio) PropylGlycosides", *Carbohydrate Research*, 37:193–201 (1974).
37. Gannon, et al., *J. Gen. Microbiol.*, 136:1125–1135 (1990)

38. Weinstein, et al., *J. Bacteriol.*, 170:4223–4230 (1988)
39. Ito, et al., *Microb. Pathog.*, 8:47–60 (1990)
40. Head, et al., *FEMS Microbiol. Lett.*, 51:211–216 (1988)
41. Schmitt, et al., *Infect. Immun.*, 59:1065–1073 (1991)
42. Scotland, et al., Lancet, ii:885–886 (1991)
43. Oku, et al., *Microb. Pathog.*, 6:113–122 (1989)
44. Boyd, et al., *Nephron*, 51:207–2210 (1989)
45. DeGrandis, et al., *J. Biol. Chem.*, 264:12520–12525 (1989)
46. Waddell, et al., *Biochem. Biophys. Res. Comm.*, 152:674–679 (1988)
47. Lingwood, et al., *J. Biol. Chem.*, 262:8834–8839 (1987)
48. Waddell, et al., *Proc. Natl. Acad. Sci. (USA)*, 87:7898–7901 (1990)
49. Cohen, et al., *J. Biol. Chem.*, 262:17088–17091 (1987)
50. Jacewicz, et al., *J. Exp. Med.*, 163:1391–1404 (1986)
51. Lindberg, et al., *J. Biol. Chem.*, 262:1779–1785 (1987)
52. Armstrong, G. D. et al., *Infect. Immunol.*, 55:1294–1299 (1987)
53. Armstrong, G. D. et al., *J. Infect. Dis.* 164:1160–1167 (1991)

The disclosure of the above publications, patents and patent application are herein incorporated by reference in their entirety to the same extent as if the language of each individual publication, patent and patent application were specifically and individually included herein.

State of the Art

Diarrhea caused by strains of pathogenic *E. coli* has been found to be associated with the production of a variety of enterotoxins. Some pathogenic *E. coli* produce enterotoxins that are closely related to the shiga toxin associated with Shigella-cause dysentery. The first member of the family of shiga-like toxins (SLT) to be isolated was cytotoxic for African Green Monkey (Vero) cells and was originally called verotoxin. Since its structural similarity to shiga toxin has been established by sequencing of the relevant genes, this toxin is now more commonly called shiga-like toxin I (SLTI) [5,6,7].

Additional members of the SLT family have subsequently been isolated that can be distinguished serologically, on the basis of gene sequence, or on host specificity [37–43]. Various types of SLTII have been described and have been assigned various designations depending on the strain of *E. coli* from which they are isolated and the host affected. Thus variants have been designated SLTII; vtx2ha; SLTIIvh; vtx2hb; SLTIIc; SLTIIvp and so forth.

All of the SLT's are multimeric proteins composed of an enzymatic (A) subunit and multiple (B) subunits. The B oligomer is the binding portion of the toxin that allows it to bind to host cell receptors. The B subunits of SLTI, SLTII and SLTIIvh recognize host cell globoseries glycolipid receptors containing at minimum the disaccharide subunit αGal(1–4)βGal at the non-reducing terminus; SLTIIvp has been shown to bind to the receptors containing this subunit but not necessarily to the non-reducing end [2, 44–51]. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLTs may cause damage that can result in renal failure and hemoglobin in the urine. SLTs are the causative agent in the hemolytic-uremic syndrome. SLTs may also be partially involved in the pathogenesis of hemorrhagic colitis (bloody diarrhea).

The hemolytic uremic syndrome (HUS) is the leading cause of acute renal failure in childhood and affects approximately 7–10% of children in the 5–10 days following infection with *E. coli* 0157:H7 and other verotoxin/shiga-like toxin producing *E. coli* (VTEC).

Recent attention regarding such pathogenic *E. coli* has focussed on the known correlation between *E. coli* contamination of certain meats and subsequent infection in humans after ingestion of this meat. The problem is particularly acute with regard to hamburger meat where ingestion of undercooked meat has been found to be the causative factor in the infection. This problem is compounded by the fact that the rapid progression of the pathogenic *E. coli* infection into HUS via the expression of the SLTs suggests the hypothesis that initial colonization of the intestinal tract is followed by endothelial injury and subsequent kidney involvement via the transmembrane delivery of the SLT toxin into the blood stream of the infected individual.

As a complicating factor, the art suggests against the use of antibiotics in the treatment of enterohemorrhagic *E. coli* infection [8]. The use of antimotility drugs also appears to be counterproductive [9].

One reported method for the treatment of such infections is to orally administer a pharmaceutically inert affinity support comprising an αGal(1→4)βGal subunit to the infected patient [10]. This support passes into the intestinal tract of the patient whereupon the αGal(1→4)βGal subunit binds the Shiga-like toxin. Subsequently, the toxin bound to this solid support is eliminated from the body as part of the stool. This procedure is one of the first, if only, reported methods for removing such toxins from the body which, in turn, inhibits manifestation of the conditions associated with toxin accumulation.

Notwithstanding the significant advances made by this reported method, further advances in the treatment of enterohemorrhagic *E. coli* infections are needed in order to reduce the occurrence of HUS and the high mortality levels associated therewith.

SUMMARY OF THE INVENTION

This invention is directed to the surprising and unexpected discovery that the clinical incidence of HUS arising from enterohemorrhagic *E. coli* infection is significantly reduced by the time critical administration of a pharmaceutical composition comprising a pharmaceutically inert affinity support comprising an αGal(1→4)βGal subunit which subunit binds the SLT. Specifically, it has been found that the clinical incidence of HUS arising from enterohemorrhagic *E. coli* infection is reduced when this pharmaceutical composition is administered within 3 days of presentation of the infection. Contrarily, administration of this pharmaceutical composition after this time frame or when organs other than the intestine are involved in the infection, substantially reduces the ability of this composition to reduce the incidence of HUS.

Accordingly, in one of its method aspects, this invention is directed to a method for inhibiting the development of hemolytic uremic syndrome in a patient arising from enterohemorrhagic *E. coli* infection mediated by shiga-like toxins which method comprises administering to said patient an effective amount of a pharmaceutical composition comprising a pharmaceutically inert affinity support comprising an αGal(1→4)βGal subunit which is bound to said support through a non-peptidyl linker arm, wherein said subunit binds SLT toxin and wherein this pharmaceutical composition is administered within about 3 days of presentation of the infection. In a preferred embodiment the pharmaceutical composition is administered to the patient prior to organ involvement other than involvement of the intestine.

For the purposes of this invention, the presentation of the infection is determined after the identification of at least one condition associated with an SLT mediate *E. coli* infection. Such conditions include, for example, patients with diarrhea and one of the following: abdominal cramping, blood in the stool, rectal prolapse, detection of a verotoxin-producing *E. coli* in the patient's stool; ingestion of food suspected of containing a verotoxin-producing *E. coli;* or close contact with an individual known to have an SLT mediated infection. Preferably, the presentation of the infection is manifested by bloody diarrhea. In a particularly preferred embodiment, the initial clinical evaluation that the individual is afflicted with an SLT mediate *E. coli* infection is confirmed via diagnostic evaluation of the stool. One diagnostic tool commercially available for detecting SLT mediated *E. coli* infection is sold by Meridian Diagnostic, Inc., Cincinnati, Ohio, USA 45244 under the name Premier EHEC.

In a further aspect, the invention provides a method for inhibiting the development of hemolytic uremic syndrome in a patient presenting an enterohemorrhagic *E. coli* infection mediated by shiga-like toxin, which method comprises administering to the patient an effective amount of a pharmaceutical composition comprising a pharmaceutically inert affinity support comprising an oligosaccharide selected from the group consisting of αGal(1→4)βGal, αGal(1→4)βGal(1→4)βGlcNAc and αGal(1→4)βGal(1→4)βGlc which oligosaccharide is bound to the support through a non-peptidyl linker arm, wherein this pharmaceutical composition is administered within about 3 days of presentation of the infection. In a preferred embodiment the pharmaceutical composition is administered to the patient prior to organ involvement other than the intestine.

DESCRIPTION OF THE PREFERRED EMBODIMENTS

As noted above, this invention relates to methods for the neutralization of shiga-like toxins (SLT) associated with enteric *E. coli* infection which methods inhibit progression of this infection into hemolytic uremic syndrome (HUS). However, prior to discussing this invention in further detail, the following terms will first be defined:

A. Definitions

As used herein the following terms have the following meanings:

The term "shiga-like toxin" or "SLT" or "verotoxin" refers to a group of toxins produced by enterohemorrhagic *E. coli* that resemble the Shigella-produced shiga toxins as is commonly understood in the art. These toxins comprise an enzymatically active A subunit and a multimeric receptor binding B subunit. Such SLTs include SLTI and the various grouped toxins designated in the art as SLTII.

Rapid tight binding of SLTs to $P_1$ disaccharide, $P_1$ trisaccharide, or $P_k$ trisaccharide is demonstrated by the verocytotoxicity neutralization assays contained herein.

The term "organ involvement" refers to clinically defined organ involvement mediated by SLTs which correlates to the natural progression of the disease. Organs other than the intestines include, by way of example, the kidney, heart, elements of the central nervous system ("CNS") (i.e., brain, spinal cord, etc.), liver, ad the like. Conventional blood chemistry tests can evaluate liver, heart, and kidney involvement whereas clinical symptoms including dementia, convulsions, disorientation, etc. are employed to determine CNS involvement.

"Hemolytic uremic syndrome" is considered to be present if there is renal injury and either hemolysis or thrombocytopenia. Renal injury requires an elevation in the serum creatinine concentration (>50 μmol/L for those less than 5 years, or >60 μmol/L for those 5–6 years) or a difference in the recorded creatinine values during the acute phase of the illness of more than 50% or at least 10 red blood cells per high power field on urine microscopy. Hemolysis is judged to be present if the hemoglobin concentration is ≦105 g/L or if there are red blood cell fragments on the smear or if a red blood cell transfusion was administered before the hemoglobin dropped to ≦105 g/L. Thrombocytopenia is defined as a platelet concentration of less than $150\times10^9$/L.

The term "biocompatible" refers to chemical inertness with respect to animal or human tissues or body fluids. Biocompatible materials are non-sensitizing.

The term "compatible linker arm" refers to a moiety which serves to space the oligosaccharide structure from the biocompatible solid support and which is bifunctional wherein one functional group is capable of covalently binding to a reciprocal functional group of the support and the other functional group is capable of binding to a reciprocal functional group of the oligosaccharide structure. Compatible linker arms preferred in the present invention are non-peptidyl linker arms. That is to say that the linker arms do not employ a peptide group to link the oligosaccharide structure to the solid support.

The term "solid support" refers to an inert, solid material to which the oligosaccharide sequences is bound via a compatible linker arm. Where use is in vivo, the solid support will be biocompatible.

The solid supports to which the oligosaccharide structures of the present invention are bound may be in the form of particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Solid supports made of inorganic materials are preferred. Preferably the solid supports have a particle size of from about 10 to 500 microns for in vivo use. In particular, particle sizes of 100 to 200 microns are preferred.

The term "SYNSORB" refers to synthetic 8-methoxycarbonyloctyl oligosaccharide structures covalently coupled to CHROMOSORB P™ (Manville Corp., Denver, Col.) [11], which is a derivatized silica particle.

Synthetic oligosaccharide sequences covalently attached to a biocompatible solid support, e.g., CHROMOSORB P™ (SYNSORB) may be used to bind SLT toxins or verotoxins. These compositions are useful to prevent HUS and associated conditions. SYNSORB is particularly preferred for these compositions because it is non-toxins and resistant to mechanical and chemical decomposition. SYNSORBs have been found to pass unaffected through the rat gastrointestinal tract. They were found to be eliminated completely and rapidly (99% eliminated in 72 hours) following oral administration. Additionally, the high density of oligosaccharide moieties on SYNSORB is particularly useful for binding verotoxin.

For the purpose of this application, all sugars are referenced using conventional three letter nomenclature. All sugars are assumed to be in the D-form unless otherwise noted, except for fucose, which is in the L-form. Further, all sugars are in the pyranose form.

Linking moieties that are used in indirect bonding are preferably organic bifunctional molecules of appropriate length (at least one carbon atom) which serve simply to distance the oligosaccharide structure for the surface of the solid support.

The compositions of this invention are preferably represented by the formula:

$$(\text{OLIGOSACCHARIDE—Y—R})_n\text{—SOLID SUPPORT}$$

where OLIGOSACCHARIDE comprises the αGal(1→4)βGal subunit and contains at least two 2 sugar units and preferably no more than 6 sugar units which oligosaccharide binds to the shiga-like toxin. Y is oxygen, sulfur or nitrogen, R is an aglycon linking arm of at least 1 carbon atom, SOLID SUPPORT is as defined above, and n is greater than or equal to 1. Preferred aglycons are from 1 to about 10 carbon atoms. Oligosaccharide sequences containing about 2 to 10 carbon atoms. Oligosaccharide sequences containing about 2 to 10 saccharide units may be used. Sequences with about 2 to 3 saccharide units are preferred. Preferably, n is such that the composition contains about 0.25 to 2.50 micromoles oligosaccharide per gram of composition.

Numerous aglycon linking arms are known in the art. For example, a linking arm comprising a para-nitrophenyl group (i.e., $—OC_6H_4pNO—$) has been disclosed [29]. At the appropriate time during synthesis, the nitro group is reduced to an amino group which can be protected as N-trifluoroacetamide. Prior to coupling to a support, the trifluoroacetamide group is removed thereby unmasking the amino group.

A linking arm containing sulfur has been disclosed [30]. Specifically, the linking arm is derived from a 2-bromoethyl group which, in a substitution reaction with thionucleophiles, has been shown to lead to linking arms possessing a variety of terminal functional groups such as $—OCH_2CH_2SCH_2CO_2CH_3$ and $—OCH_2CH_2SC_6H_4—pNH_2$. These terminal functional groups permit reaction to complementary functional groups on the solid support, thereby forming a covalent linkage to the solid support. Such reactions are well known in the art.

A 6-trifluoroacetamido-hexyl linking arm ($—O—(CH_2)_6—NHCOCF_3$) has been disclosed [31] in which the trifluoroacetamide protecting group can be removed, unmasking the primary amino group used for coupling.

Other exemplifications of known linking arms include the 7-methoxycarbonyl-3,6,dioxaheptyl linking arm [32] ($—OCH_2CH_2)_2OCH_2CO_2CH_3$); the 2-(4-methoxycarbonylbutancarboxamide)ethyl [33] ($—OCH_2CH_2NHC(O)(CH_2)_4CO_2CH_3$); the allyl linking arm [34] ($—OCH_2CH=CH_2$) which, by radical co-polymerization with an appropriate monomer, leads to co-polymers; other allyl linking arms [35] are known ($—O(CH_2CH_2O)_2CH_2CH=CH_2$). Additionally, allyl linking arms can be derivatized in the presence of 2-aminoethanethiol [36] to provide for a linking arm $—OCH_2CH_2CH_2SCH_2CH_2NH_2$. Other suitable linking arms have also been disclosed [12–14, 16, 17].

Preferably, the aglycon linking arm is a hydrophobic group and most preferably, the aglycon linking arm is a hydrophobic group selected from the group consisting of $—(CH_2)_8C(O)—$, $—(CH_2)_5OCH_2CH_2CH_2—$ and $—(CH_2)_8CH_2O—$. Non-peptidyl linking arms are preferred for use as the compatible linking arms of the present invention.

The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable, for example, due to questionable stability in the gastrointestinal tract when given orally.

The compositions useful in the conduct of the methods of the invention comprise the αGal(1–4)βGal disaccharide subunit which subunit can be used alone or in conjunction with a higher oligosaccharide, e.g., the αGal(1–4)βGal(1–4)βGlcNAc trisaccharide or the αGal(1–4)βGal(1–4)βGlc trisaccharide. The αGal(1–4)βGal disaccharide subunit is preferably found at the non-reducing terminus of an oligosaccharide.

The oligosaccharide is coupled to a solid support or coupled directly, preferably through a linking arm such as that described by Lemieux et al. [11]. The di and trisaccharide units may also be coupled directly to pharmaceutically acceptable carriers or constitute a portion of an oligosaccharide coupled to such carriers.

B. Synthesis

Chemical methods for he synthesis of oligosaccharide structures can be accomplished by methods known in the art. These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [12–28].

The oligosaccharide structure(s) is covalently bound or noncovalently (passively) adsorbed onto the solid support. The covalent bonding may be via reaction between functional groups on the support and the compatible linker arm of the oligosaccharide structure.

The inert affinity supports comprising an αGal(1→4)βGal subunit which is bound to said support through a non-peptidyl linker arm used in the methods of this invention are made by methods known in the art [11, 12] as follows. In each case the 8-methoxycarbonyloctyl glycoside of the respective hapten is activated and ligated to a silylaminated solid support, wherein the matrix is comprised of $SiO_2$, followed by the acetylation of the remaining amine groups on the solid support. These formulations are:

$P_1$-di, which contains at least 0.06 μmol/g αGal(1–4)βGal disaccharide;

$P_1$-tri, which contains at least 0.91 μmol/g αGal(1–4)βGal (1–4)βGlcNAc trisaccharide; and $P_k$-tri, which contains at least 0.74 μmol/g αGal(1–4)βGal (1–4)βGlc trisaccharide.

C. Pharmaceutical Compositions

The methods of this invention are achieved by using pharmaceutical compositions comprising one or more oligosaccharide structure, which bind SLT toxin and/or verotoxin, attached to a solid support.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art.

Compositions which may be mixed with semisolid foods such as applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The SYNSORB itself may also be used without the addition of inert pharmaceutical carriers, particularly for use in capsule form. When a pharmaceutically inert carrier is employed the carrier is typically employed in the amount ranging from about 1 to about 99 percent based on the total weight of the composition and more preferably from about 75 to about 95 weight percent.

Doses are selected to provide neutralization and elimination of SLT toxin and/or elimination of E. coli found in the gut of the affected patient. Preferred doses are from about 0.25 to 1.25 micromoles of oligosaccharide/kg body weight/day, more preferably about 0.5 to 1.0 micromoles of oligosaccharide/kg body weight/day. Using the SYNSORB compositions described above, this means about 0.5 to 1.0 gram SYNSORB/kg body weight/day, which gives a concentration of SYNSORB in the gut of about 20 mg/ml. Administration is expected to be 2 to 4 times daily, preferably for a period of one week. The specific dose level and schedule of administration will, of course, vary for each individual depending on factors such as the particular oligosaccharide structure employed, the age and condition of the subject, the extent of the disease condition, all of which are well within the skill of the art.

Administration of the oligosaccharide-containing compositions of the present invention during a period of up to seven days will be useful in treating SLT-associated diarrhea and associated conditions.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid composition should preferably contain about 1 micromole oligosaccharide/ml.

D. Methodology

SLT toxin may be neutralized by oligosaccharide sequences comprising the αGal(1→4)βGal subunits which sequences bind the toxin. In particular, such oligosaccharide sequences covalently attached to solid supports via non-peptidyl compatible linker arms have been found to neutralize SLT toxin effectively. Examples of such compositions are certain SYNSORBs, which bind and neutralize SLT toxin activity.

The ability of several oligosaccharide sequences attached to Chromosorb P via an 8-methoxylcarbonyloctyl (MCO) spacer arm to neutralize SLT toxin has been tested.

The oligosaccharide sequences attached to solid supports useful in the present invention include those which bind SLT toxin. The binding affinity of an oligosaccharide to SLT toxin is readily detectable by a simple in vitro test, as for example, set forth in Example 1 below. For the purposes of this invention, oligosaccharide sequences attached to solid supports which bind SLT toxin means those compositions which reduce endpoint titers from cytotoxic activity in vero cell assays by at least 50% and preferably by at least 95%, using the assay set forth in the Examples section.

Other oligosaccharide sequences attached to solid supports useful in the present invention are those which can bind SLT toxin significantly better ($p \leq 0.05$, using appropriate standard statistical methods, such as the Wilcoxon or Student's T-test) than a control support that does not contain any attached oligosaccharide sequences (e.g., CHROMOSORB P).

The effect of the compositions of the invention in neutralizing SLTs can be measured by comparing activity of the SLT with and without treatment with the compositions. Activity of the SLTs can be assayed by taking advantage of the toxicity of these compounds to Vero cells. Vero cells (ATCC CCL81) can be obtained from the American Type Culture Collection, Rockville, Md.

In the methods of this invention, it has been found that the clinical incidence of HUS arising from enterohemorrhagic E. coli infection is reduced when the pharmaceutical compositions described above are administered within 3 days of presentation of the infection and prior to organ involvement other than intestinal involvement. Contrarily, administration of this pharmaceutical composition after this time frame when organs other than the intestine are involved in the infection substantially reduces the ability of this composition to reduce the incidence of HUS.

Preferably, the initial clinical evaluation that the individual is afflicted with an SLT mediated E. coli infection is confirmed via diagnostic evaluation of the stool. One diagnostic tool commercially available for detecting SLT mediated E. coli infection is sold by Meridian Diagnostic, Inc., Cincinnati, Ohio, USA 42544 under the name Premier EHEC.

As can be appreciated from the disclosure above, the present invention has a wide variety of applications. Accordingly, the following examples are offered by way of illustration and not by way of limitation.

EXAMPLES

In the examples below, all temperatures are given in degrees Celsius and the following abbreviations have the following meanings. If not defined below, then the abbreviations have their art recognized meanings.

ASA=acetylated silylaminated hydrophobic 8-methoxycarbonyloctyl linkage arm
BSA=bovine serum albumin
cm=centimeter
dpm=decays per minute
EDTA=ethylene diamine tetraacetic acid
g=gram
HUS=hemolytic uremic syndrome
kg=kilogram
L=liter
LPS=lipopolysaccharide
M=molar
MEM=minimal Eagles medium
mg=milligrams
mL=milliliters
min.=minutes
mm=millimeters
nm=nanometers
PBS=phosphate buffered saline
pg=picogram
SDS=sodium dodecyl sulfate
SLT=shiga-like toxin
μg=microgram
μL=microliter
μmol=micromol In the examples below, Examples 1–3 are from Armstrong, et al. [10] and are included herein to establish that oligosaccharides comprising a αGal(1→4)βGal subunit possess similar in vitro properties. Example 4 below illustrates in vivo results for the $P_k$ trisaccharide and demonstrates the affect of timing of administration of the composition in reducing the incidence of HUS.

Example 1

SYNSORB—Verotoxicity Neutralization Assays

E. coli strains 0157:H-(E32511), which produces SLTII/SLTIIc and 026:H11(H19) which produces SLTI only or stain C600(933W), which produces SLTII only, were grown overnight at 37° C. on tryptic soy broth (Difco, Detroit, Mich.) agar plates. Polymyxin and lysozyme extracts were prepared as described previously [1,2].

The first neutralization assay was designed to test the ability of SYNSORBs to absorb SLT activity from the E. coli extracts for 30 min. at room temperature in 1.5 mL microcentrifuge tubes (Fisher) with 2 to 50 mg SYNSORB on an end-over-end rotator. The tubes were then removed from the apparatus and after the SYNSORB had settled to the bottom (a few seconds), serial five-fold dilutions of the absorbed extracts were prepared in unsupplemented MEM. Twenty (20) μL of each dilution was added to the appropriate wells in 96 well microtiter plates containing Vero cells. Bacterial extracts to which no SYNSORB was added served as controls. Once cytotoxic effects became apparent (2 to 3 days in the incubator) the growth medium was aspirated from each of the wells and Vero cells which remained viable were fixed with 95% methanol and stained with Giemsa stain (Fisher). The results were then recorded using a microtiter plate reader set at a wavelength of 620 nm as described previously [3]. The absorbance data were then plotted versus the logarithm of the extract dilution. The dilution of the extracts resulting in 50% destruction ($CD_{50}$) of the monolayers was determined by extrapolation from the resulting Vero cell killing curves. Individual experiments were always performed in duplicate and unless otherwise indicated, repeated at least two times. The percentage of neutralization was computed from the equation: 100−(100 [$CD_{50}$ oligosaccharide SYNSORB-treated extracted+$CD_{50}$ acetylated silyl-aminated (ASA) SYNSORB-treated extract]). The non-parametric Mann-Whitney test using the two-tailed statistic T was employed to compute the significance level of difference between groups of independent observations [4].

The second neutralization assay (co-incubation assay) was designed to test the ability of $P_k$ trisaccharide SYNSORB to protect Vero cells from SLT activity over 3 days at 37° C. This assay involved incubating 180 μL of serial five-fold dilutions of polymyxin extracts in ethylene oxide-sterilized 1.5 mL microcentrifuge tubes each containing 2, 5 or 10 mg of $P_k$ trisaccharide SYNSORB. After 1 hour incubation with the SYNSORB, the entire contents of each microcentrifuge tube were added to Vero cells monolayers in microtiter plates prepared as described above. The microtiter plates were then incubated at 37° C. for 3 days and the results of the experiment were recorded as described above (FIGS. 1 and 2).

Figure 1A:
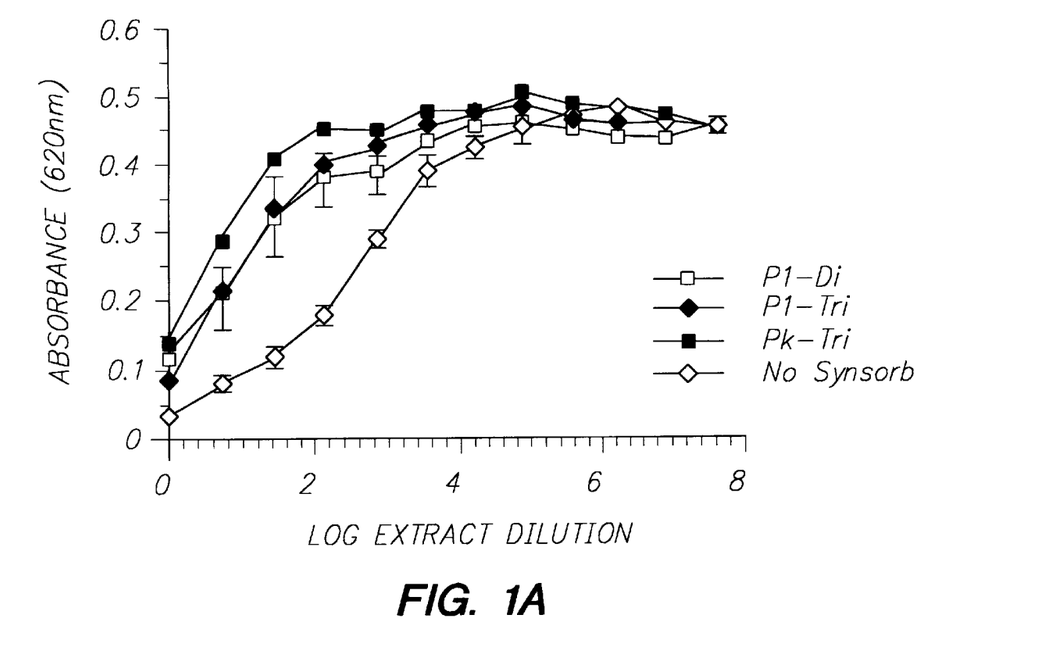
FIGS. 1A and B demonstrate the toxicity of bacterial extracts obtained using polymyxin-B with respect to their ability to kill Vero cells in the presence and absence of various SYNSORBs.
Figure 1B:
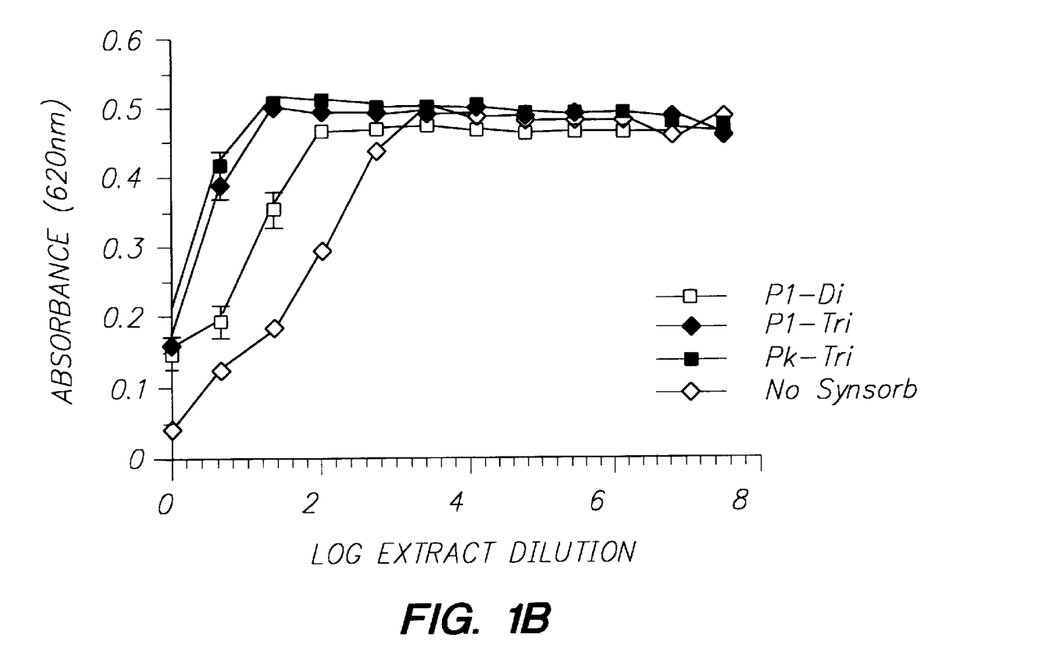
Figure 2A:
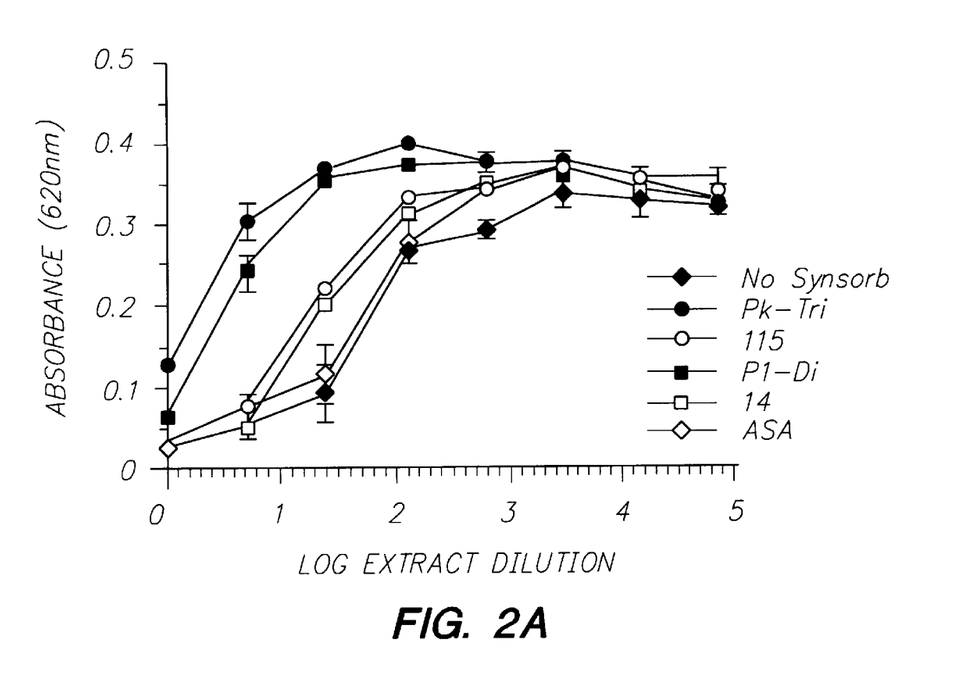
FIGS. 2A and B demonstrate the toxicity of bacterial extracts obtained using lysozyme with respect to their ability to kill Vero cells in the presence and absence of various SYNSORBs.
Figure 2B:
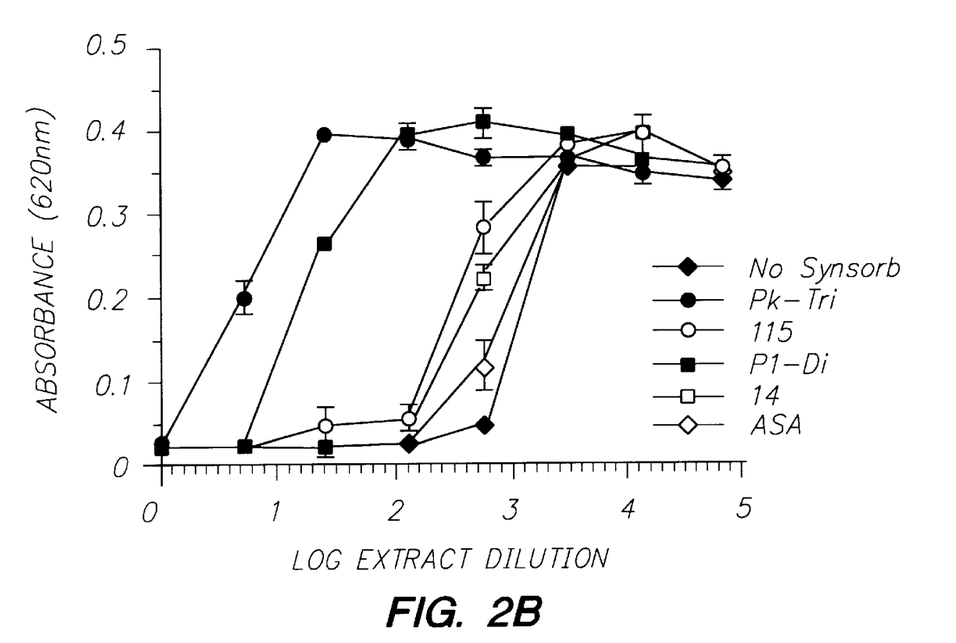
Figure 3A:
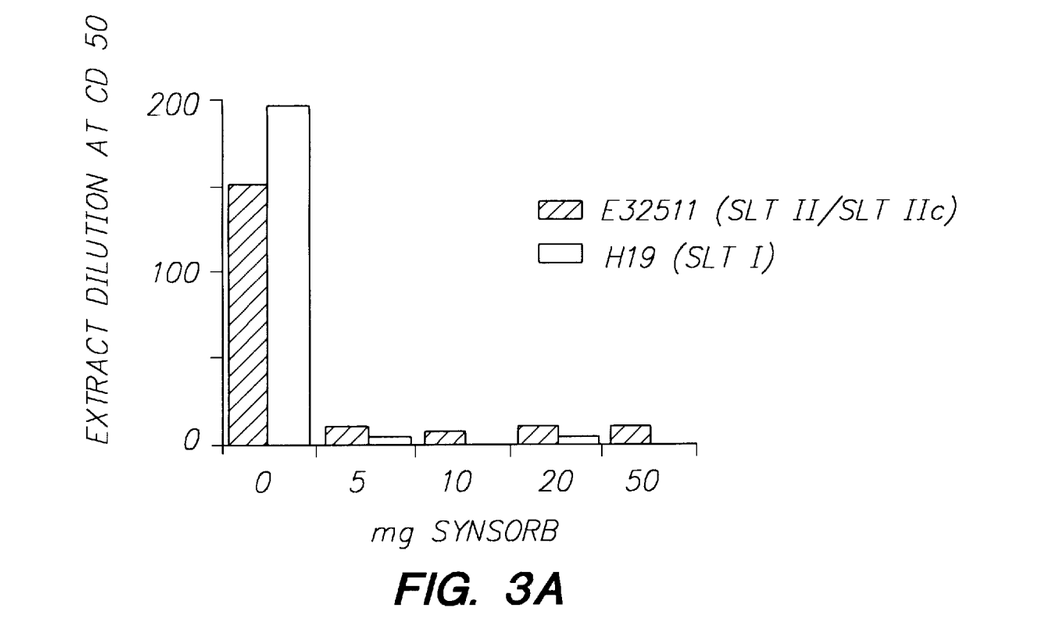
FIG. 3A demonstrates that as little as 10 mg of $P_k$ trisaccharide SYNSORB removes >90% of SLT toxins from bacterial extracts.
Figure 3B:
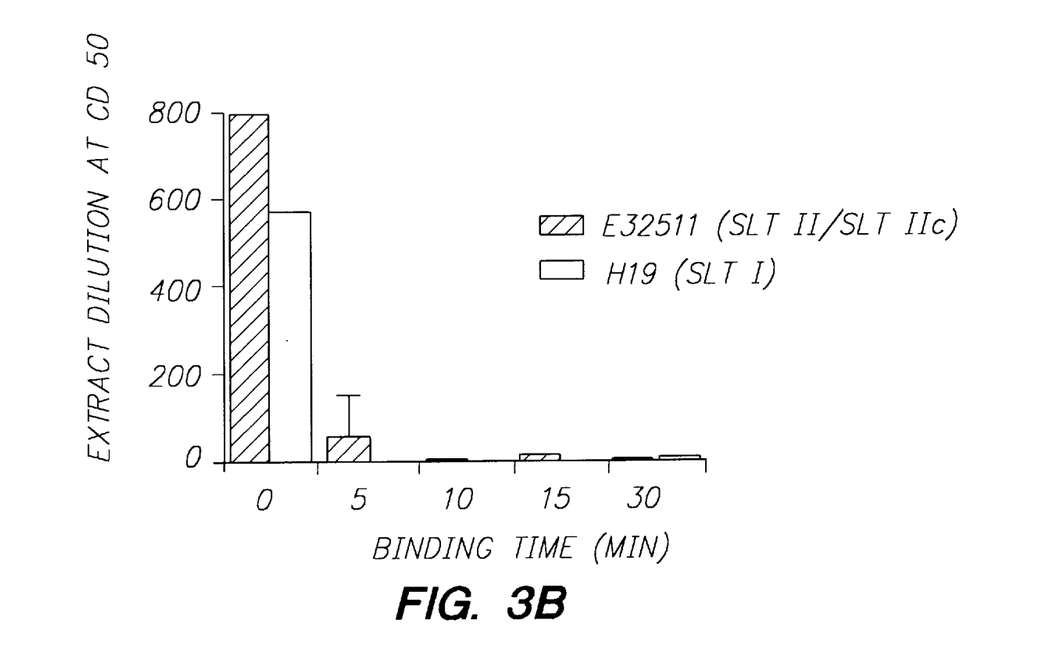
FIG. 3B demonstrates that the binding of the SLT toxins occured within 5 minutes of mixing extracts with the $P_k$ SYNSORB.

The foregoing determination was repeated using varying amounts of $P_k$-tri and various times of incubation, with the results shown in FIGS. 3A and 3B. As shown in FIG. 3A, as little as 5 mg SYNSORB was capable of neutralizing the activity of the extracts of both E32511 and H19 strains; similarly, as shown in FIG. 3B, only about 5 min. incubation was required to achieve this result in either extract.

Example 2

Iodinated SLTI Binding Assay

Purified SLTI was iodinated in 12×75 mm acid-washed glass culture tubes coated with 40 μg of Iodo Gen (Pierce Chemical Co., Rockford, Ill., USA). About 6 μg of purified SLTI was incubated for 1 min. with 20 MBq $^{125}$-I labeled sodium iodide in 100 μL of PBS. The reaction mixture was passed through a glass wool-plugged Pasteur pipette into 200 μL PBS containing a solution of cysteine (1 mg/mL) in PBS as described by Armstrong, G. D. et al. [52] After 1 min., 200 μL of PBS containing 1% BSA was added to the mixture and the iodinated SLTI was purified by passing the solution through a 1 cm×30 cm Sephadex-G 25 gel filtration column with 0.1% BSA in PBS. The efficiency of the iodination reaction was determined by measuring the number of counts that were incorporated into trichloroacetic acid precipitated protein. Aliquots of the iodinated SLTI was stored at −90° C.

The assays were performed in PBS containing 0.15% BSA to reduce nonspecific binding. 2 mg of the SYNSORB were incubated for 30 min. on an end-over-end rotator with approximately 20,000 dpm of the iodinated SLTI prepared above (specific activity, $2.2 \times 10^7$ dpm/µg, $CD_{50}$ in the Vero-cytotoxicity assay, 0.4 pg/mL), in 0.5 mL PBS/BSA). The SYNSORB was then washed with 3×1 mL portions of PBS/BSA to remove unbound counts. The derivatized SYNSORB were counted in an LKB Rackgamma model 1270 Gamma Counter. Similarly, ASA was also employed to determine the effect of using this material.

The results are shown in Table 1.

TABLE 1

| SYNSORB | % SLTI Bound |
|---|---|
| Pk-tri | 93 |
| ASA | 5 |

Figure 4:
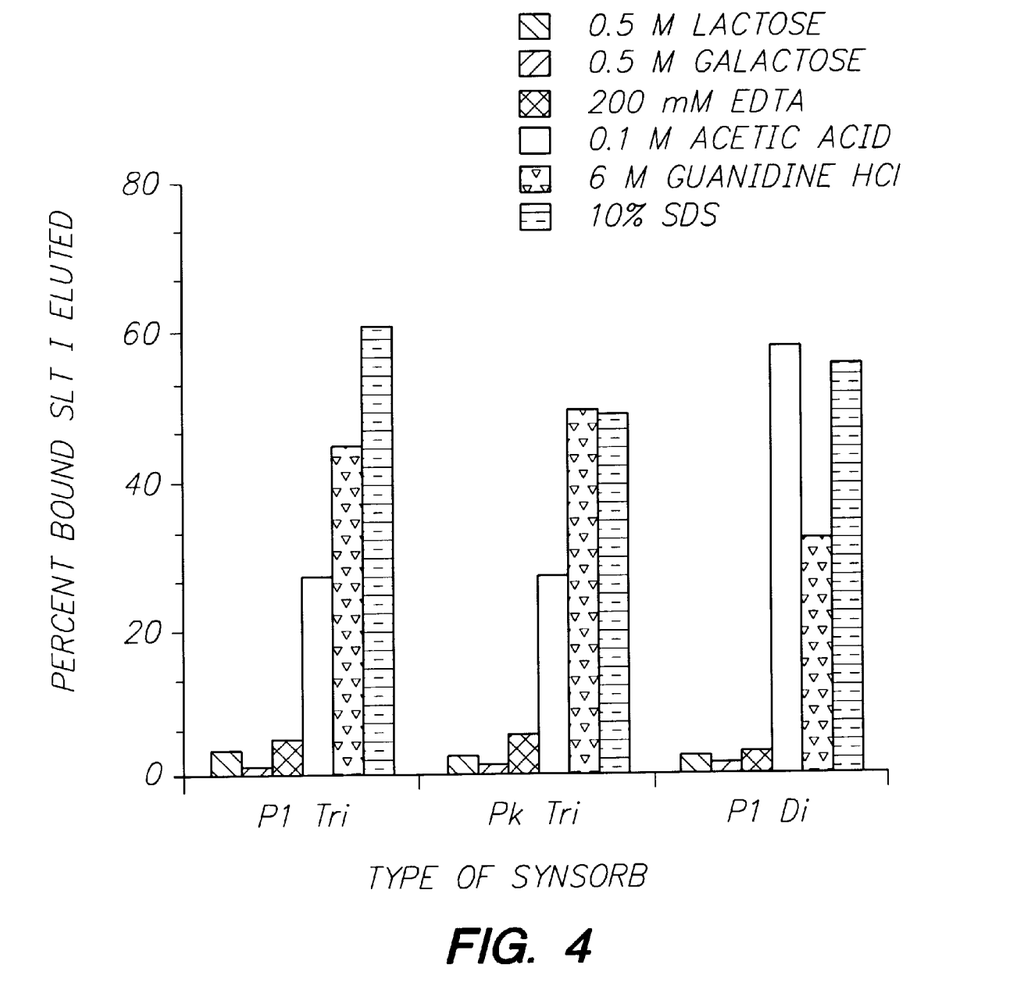
FIG. 4 demonstrates that difficulty in eluting the bound $I^{125}$ labelled SLTI from various SYNSORBs utilizing a variety of eluants.

The SLT bound to $P_k$-tri SYNSORB could be partially released using 0.1 M acetic acid, 6 M guanidine HCl, or by heating in boiling water bath for 30 min. in 10% SDS. However, weight 0.5 M lactose, 0.5 M galactose, or 0.2 M EDTA could displace the bound SLTI (FIG. 4).

Figure 5:
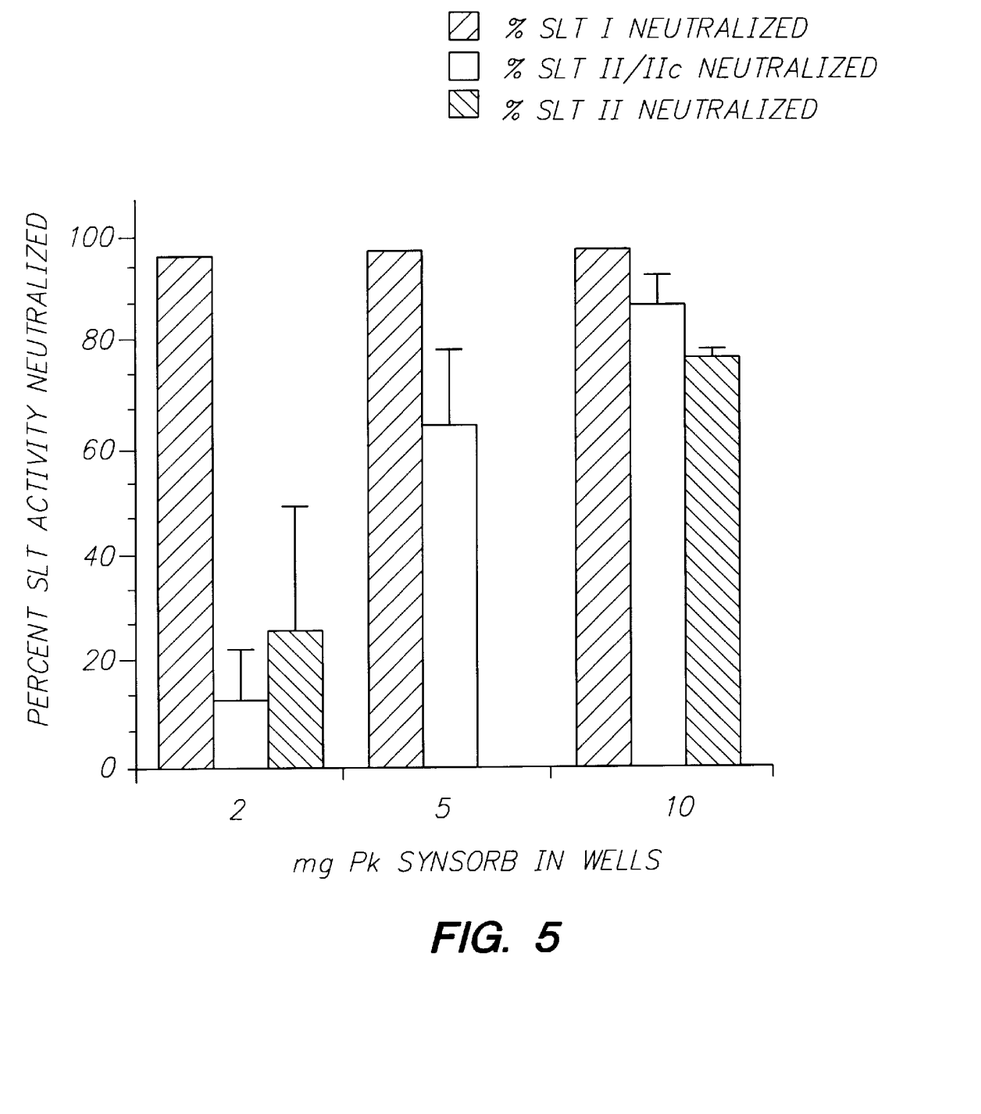
FIG. 5 demonstrates that >90% SLTI, SLTII/IIc and SLTII activity was neutralized by co-incubation of Vero cells and SLT extracts for three days, with as little as 10 mg of $P_k$ trisaccharide SYNSORB.

Subsequent experiments showed that 2 mg of $P_k$-tri neutralized approximately 90% of the activity in *E. coli* H19 (SLTI) but about 10 mg Pk-tri SYNSORB was required to neutralize the activity of the *E. coli* 32511 (SLTII/SLTIIc) or *E. coli* C600/933W (SLTII) to a similar extent (FIG. 5).

Example 3

Performance Under Digestive Tract Conditions $P_k$ trisaccharide SYNSORB was incubated for the various times at 37° C. in 0.01 M HCl to simulate conditions in the stomach, then washed extensively in PBS to remove the HCl. The HCl-treated SYNSORB was then tested for SLTI and SLTII neutralizing activity in the Vero cytotoxicity assay as described hereinabove, and by Armstrong, G. D. et al. [53].

Briefly, *E. coli* 026:H11 (SLTI) or 0157:H (SLTII) were grown overnight at 37° C. on Tryptic Soy Agar (TSA). The bacteria from 5 plates were harvested in 3.0 mL PBS containing 0.1 mg/mL Polymyxin B sulfate. The resulting suspension was then clarified by centrifugation.

Five mg of $P_k$ trisaccharide SYNSORB were missed with approximately 1 mL of polymyxin extract of the bacterial strains listed in the table below. Data represent the average of two independent determinations, each performed in duplicate. Values in brackets give the range for each value.

TABLE 2

Ability of HCl-Treated $P_k$ Trisaccharide SYNSORB to Neutralize SLT Activity in the Vero Cell Assay

| HCl | Percent SLT Activity Neutralized | | |
|---|---|---|---|
| Incubation Time (Hours at 37° C.) | 026:H11 (SLTI) | 0157:H7 (SLTII/IIc) | C600 (SLTII) |
| 0 | 94 (4) | 88 (5) | 55 (10) |
| 1 | 94 (6) | 80 (2) | 66 (5) |
| 4 | 96 (5) | 91 (8) | 73 (2) |
| 18 | 94 (6) | 93 (6) | 70 (7) |

As shown in Table 2, incubation with HCl does not appreciably diminish neutralizing activity. To simulate intestinal conditions, various SYNSORBs were incubated for 2 hours at 37° C. in buffer or in rat intestinal sacs. The incubated SYNSORBs were assayed for neutralizing activity against SLTI and SLTII, generally as described above. Briefly, SYNSORBs recovered from the rat intestines were sonicated for 30 to 60 seconds in a Branson Model B-220 Ultrasonic Cleaner to disrupt clumps of aggregated material. The sonicated SYNSORBs were then washed 4 times with 5 mL of double distilled, deionized $H_2O$ and dried under vacuum. Control SYNSORBs were treated in a similar manner. The polymyxin-extract described above was diluted to 8 mL with PBS. Five mg of SYNSORB was added to 0.9 mL portions of the diluted polymyxin extract. These were then incubated at room temperature for 1 hour on an end-over-end rotator. The resulting supernatant solutions were analyzed for SLTI or SLTII activity. Percent neutralization was calculated relative to the $CD_{50}s$ of polymyxin extracts incubated with the ASA control SYNSORB. These results are shown in Tables 3–6.

Table 3 shows the results of neutralization of SLTI activity by SYNSORB incubated in buffer; Table 4 shows neutralization of SLTI activity by SYNSORB incubated in intestinal sacs; Table 5 shown neutralization of SLTII activity by SYNSORB incubated in buffer; and Table 6 shows neutralization of SLTII activity by SYNSORB incubated in rat intestinal sacs.

TABLE 3

| SYNSORB | Percent SLTI Activity Neutralized[a] |
|---|---|
| ASA SYNSORB[b] | 0 |
| $P_1$ Disaccharide | 93 (88–97) |
| $P_1$ Trisaccharide | 98 (96–100) |

[a]Average of duplicate determinations. Range in brackets.
[b]Control SYNSORB containing only the acetylated silylaminated (ASA) hydrophobic 8-methoxycarbonyloctyl linkage arm.

TABLE 4

| SYNSORB | Percent SLTI Activity Neutralized[a] |
|---|---|
| ASA SYNSORB[b] | 0 |
| $P_1$ Disaccharide | 82 ± 6 |
| $P_1$ Trisaccharide | 98 ± 2 |

[a]Average of triplicate determinations ± standard deviation of the mean.
[b]Control SYNSORB containing only the acetylated silylaminated (ASA) hydrophobic 8-methoxycarbonyloctyl linkage arm.

TABLE 5

| SYNSORB | Percent SLTI Activity Neutralized[a] |
|---|---|
| ASA SYNSORB | 0 |
| $P_1$ Disaccharide | 84 |
| $P_1$ Trisaccharide | 98 |

[a]Results of one determination.

TABLE 6

| SYNSORB | Percent SLTI Activity Neutralized[a] |
|---|---|
| ASA SYNSORB | 0 |
| $P_1$ Disaccharide | 65 ± 9[a] |
| $P_1$ Trisaccharide | 96[b] |

[a]Average of triplicate determinations ± standard deviation of the mean.
[b]Results of one determination.

As shown above, neither the conditions of the stomach nor those of the small intestine are detrimental to the activity of the derivatized SYNSORBs in neutralizing SLTI or SLTII.

Example 4

Performance in Human Patients

Pharmaceutical compositions comprising $P_k$ SYNSORB was administered to children at 13 Canadian sites.

To allow treatment at the earliest possible point in the gastrointestinal illness, children were eligible for inclusion in this study before the results of stool cultures were known. Children were limited to the ages of from 6 months to 15 years of age. The children were eligible for the study if they had diarrhea (had passed at least 2 loose stools in the preceding 24 hours) and one of the following: abdominal cramping, blood in the stools, rectal prolapse, close contact with an individual with known VTEC infection or HUS, or E. coli 0157:H7 cultured from the stool. Patients were excluded if they had chronic renal or hematologic disease or if they had evidence of hemolysis, renal injury or thrombocytopenia on either an actuate or chronic basis, if they had chronic bowel disease, if they had an encephalopathy that would preclude ingestion of oral medication or if they were receiving anticonvulsant medications or pancreatic enzyme supplements. Patients remained in the study unless stool cultures identified a non-VTEC stool pathogen.

A complete blood count, peripheral blood smear, serum urea and creatinine urinalysis and serum for anti-0157 antibodies was obtained from all subjects prior to enrollment. Serum samples from enrollment and day 60 after enrollment were tested for anti-0157 LPS antibodies using a passive hemagglutination assay. An anti-0157 LPS titer of >1:500 was considered consistent with recent infection.

Stool samples from all patients were submitted at entry to the hospital microbiology laboratory and were routinely inoculated onto a modified sorbitol-MacConkey agar. Colonies which failed to ferment sorbitol were identified as E. coli by standard biochemical tests, and isolates were serogrouped by agglutination using 0157 antisera. Stool samples from those with negative routine cultures were forwarded to the National Laboratory for Enteric Pathogens at the Center for Disease Control in Ottawa, Canada. These samples were evaluated for the presence of other verotoxin-producing E. coli.

Eligible subjects were stratified on the basis of age and center and then randomized. Patients received either SYNSORB-Pk mixed in baby food or an equal volume of ground corn meal placebo with similar taste and texture. The primary outcome of interest was the proportion of patients with evidence of HUS at day seven of treatment.

The study drug was administered twice daily for seven days. The dose of SYNSORB-Pk was approximately 500 mg/kg/day. The placebo was ground corn meal, selected because it had a mildly gritty texture similar to SYNSORB-Pk and like SYNSORB-Pk had no taste. To improve palatability, both SYNSORB-Pk and the corn meal placebo were mixed in a commercially available baby food (fruit). If a dose was vomited within 30 minutes, it was readministered. Subjects continued to receive the study drug for seven days if their stool culture results identified E. coli 0157 or if no bacterial pathogen was identified. If the stool culture identified an alternate cause for symptoms, such as Salmonella, Shigella, Campylobacter or Yersinia species, the subject stopped taking the medication.

The primary outcome measure for the trial was the proportion of subjects with hemolytic uremic syndrome by the time of laboratory re-evaluation 8–10 days after enrollment. Hemolytic uremic syndrome was considered to be present if there was renal injury and either hemolysis or thrombocytopenia. Renal injury required an elevation in the serum creatinine concentration (>50 $\mu$mol/L for those less than 5 years, or >60 $\mu$mol/L for those 5–6 years) or a difference in the recorded creatinine values during the acute phase of the illness of more than 50% or at least 10 red blood cells per high power field on urine microscopy. Hemolysis was judged present if the hemoglobin concentration was $\leq$105 g/L or if there were red blood cell fragments on the smear or if a red blood cell transfusion was administered before the hemoglobin dropped to $\leq$105 g/L. All peripheral blood smears were forwarded to the central study laboratory at the Children's Hospital of Eastern Ontario in Ottawa, where they were graded by laboratory technicians blinded to the treatment status of the subject.

Thrombocytopenia was defined as a platelet concentration of less than $150 \times 10^9$/L. Mild HUS was present if the peak elevation in creatinine concentration was less than 100 $\mu$mol/L; moderate HUS required a creatinine concentration of 101–400 $\mu$mol/L and dialysis less than seven days; severe HUS required creatinine concentration of above 400 $\mu$mol/L or dialysis for seven or more days or death. In addition to these primary outcomes, patients were also classified as having the secondary outcomes of isolated hemolytic anemia, isolated thrombocytopenia, or isolated renal injury as defined earlier. Parents recorded in a daily diary the frequency of diarrhea and vomited doses of medication as well as the frequency of possible adverse events.

The results of this evaluation were analyzed to determine the effect of this protocol on those patients with a verified SLT mediated pathogenic E. coli infection and who were compliant with the treatment regiment. The analysis of these results were divided into two groups, i.e., those treated within three days of first presenting symptoms of E. coli infection and those treated after three days of first presenting symptoms of E. coli infection. Tables 7 and 8 below set forth the results of this evaluation.

TABLE 7

Outcome by Group - Those only with E. coli or stool positive cases and treated $\leq$ 3 days post syndrome

| | SYNSORB | | PLACEBO | |
|---|---|---|---|---|
| | No. of cases | % | No. of Cases | % |
| Normal | 24 | 64.9 | 20 | 58.8 |
| Isolated thrombo | — | | — | |
| Non-anemic hemolysis | 1 | 2.7 | 2 | 5.9 |
| Hemolytic anemia | 1 | 2.7 | — | |
| Renal Insufficiency | 5 | 13.5 | 2 | 5.9 |
| Mild HUS | 4 | 10.8 | 6 | 17.6 |
| Moderate HUS | — | | 2 | 5.9 |
| Severe HUS | 1 | 2.7 | 2 | 5.9 |
| Alternate pathogen | — | | — | |
| Adverse event | — | | — | |
| Missing lab values | 1 | 2.7 | — | |
| Non-compliant | — | | — | |
| RA error | — | | — | |
| TOTAL | 37 | | 34 | |

TABLE 8

Outcome by Group - Those only with *E. coli* or stool positive cases and treated > 3 days post syndrome

|  | SYNSORB | | PLACEBO | |
| --- | --- | --- | --- | --- |
|  | No. of cases | % | No. of Cases | % |
| Normal | 12 | 50.0 | 16 | 66.7 |
| Isolated thrombo | — | | 1 | 4.2 |
| Non-anemic hemolysis | 1 | 4.2 | 1 | 4.2 |
| Hemolytic anemia | 4 | 16.7 | — | |
| Renal Insufficiency | 3 | 12.5 | 2 | 8.3 |
| Mild HUS | 2 | 8.3 | 1 | 4.2 |
| Moderate HUS | 1 | 4.2 | 2 | 8.3 |
| Severe HUS | 1 | 4.2 | — | |
| Alternate pathogen | — | | — | |
| Adverse event | — | | — | |
| Missing lab values | — | | 1 | 4.2 |
| Non-compliant | — | | — | |
| RA error | — | | — | |
| TOTAL | 24 | | 24 | |

The above results demonstrate that when a patient with disease symptoms attributable to an SLT mediated *E. coli* infection is treated within three days of presentation of these symptoms, the overall incidence of HUS in the treated patients is 13.5% as compared to the overall incidence of 29.4% for placebo treated patients or a relative reduction in risk of 54.1%. The above results further demonstrate that when a patient with disease symptoms attributable to an SLT mediated *E. coli* infection is treated after three days of presentation of these symptoms, there is no relative reduction in risk for development of HUS as compared to placebo.

Accordingly, these results demonstrate the criticality of early intervention in the SLT mediated *E. coli* infection via the methods of this invention.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

What is claimed is:

1. In an improved method for treating a patient presented with enterohemorrhagic *E. coli* infection mediated by shiga-like toxins by administering to said patient an effective amount of a pharmaceutical composition comprising a pharmaceutically inert affinity support comprising an αGal(1→4)βGal subunit which is bound to said support through a non-peptidyl linker arm, wherein said subunit binds SLT toxin wherein the improvement comprises administering said pharmaceutical composition prior to the development of hemolytic uremic syndrome in the patient.

2. The method of claim 1 wherein the linker arm comprises from 1 to 10 carbon atoms.

3. The method of claim 2 wherein the linker arm is —(CH$_2$)$_8$C(O)—.

4. The method of claim 1 wherein the solid inert affinity support is silica.

5. The method of claim 1 wherein the pharmaceutical composition is administered to the patient prior to organ involvement other than intestinal involvement.

6. In an improved method for treating a patient presented with enterohemorrhagic *E. coli* infection mediated by shiga-like toxin by administering to the patient an effective amount of a pharmaceutical composition comprising a pharmaceutically inert affinity support comprising a di- or tri-saccharide selected form the group consisting of αGal(1→4)βGal, αGal(1→4)βGal(1→4)βGlcNAc and αGal(1→4)βGal(1→4)βGlc wherein said saccharide is bound to the support through a non-peptidyl linker arm, wherein the improvement comprises administering said pharmaceutical composition prior to the development of hemolytic uremic syndrome in the patient.

7. The method of claim 6 wherein said oligosaccharide sequence is αGal(1→4)βGal.

8. The method of claim 6 where said oligosaccharide sequence is αGal(1→4)βGal(1→4)βGlcNAc.

9. The method of claim 6 where said oligosaccharide sequence is αGal(1→4)βGal(1→4)βGlc.

10. The method of claim 6 wherein the linker arm comprises from 1 to 10 carbon atoms.

11. The method of claim 10 wherein the linker arm is —(CH$_2$)$_8$C(O)—.

12. The method of claim 6 wherein the solid inert affinity support is silica.

13. The method of claim 6 wherein the pharmaceutical composition is administered to the patient prior to organ involvement other than intestinal involvement.

* * * * *